United States Patent
Porper et al.

(12)

(10) Patent No.: US 6,401,288 B1
(45) Date of Patent: Jun. 11, 2002

(54) MECHANICAL TOOTHBRUSH WITH OPPOSED DUAL HEADS AND HAVING OSCILLATORY MOVEMENT

(76) Inventors: Robert P. Porper, Mill Pond Offices, 293 Rte. #100, Suite #200, Somers, NY (US) 10589; Robert G. Dickie, 15 Valley Trail, Newmarket, Ont (CA), L3Y 4V8

(*) Notice: Subject to any disclaimer, the term of this patent is extended or adjusted under 35 U.S.C. 154(b) by 0 days.

(21) Appl. No.: 09/510,501

(22) Filed: Feb. 22, 2000

Related U.S. Application Data

(63) Continuation-in-part of application No. 09/296,631, filed on Apr. 23, 1999, now Pat. No. 6,138,310.

(51) Int. Cl.[7] .............................................. A46B 13/02
(52) U.S. Cl. ........................................ 15/22.1; 15/167.2
(58) Field of Search ............................... 15/22.1, 167.2

(56) References Cited

U.S. PATENT DOCUMENTS

| | | | |
|---|---|---|---|
| 4,131,967 A | * | 1/1979 | Northemann |
| D259,977 S | | 7/1981 | Porper |
| 5,027,463 A | | 7/1991 | Daub |
| 5,259,083 A | | 11/1993 | Stansbury, Jr. |
| 5,327,607 A | | 7/1994 | Wagner |
| 5,353,460 A | | 10/1994 | Bauman |
| 5,359,747 A | | 11/1994 | Amakasu |
| 5,842,244 A | * | 12/1998 | Hilfinger ............... 15/22.1 |
| 5,842,249 A | * | 12/1998 | Sato ................... 15/167.2 |

FOREIGN PATENT DOCUMENTS

| | | | | |
|---|---|---|---|---|
| DE | 004402366 | * | 6/1994 | .............. 15/22.1 |
| JP | 4215705 | | 8/1992 | |

* cited by examiner

Primary Examiner—Randall E. Chin
(74) Attorney, Agent, or Firm—Marks & Clerk

(57) ABSTRACT

An electric toothbrush is provided with an electric motor and a driving mechanism. The driving mechanism includes a motion translation means to convert rotary motion to oscillatory movement of a drive shaft adapted to be received on the brush head portion of the electric toothbrush, so as to impart an oscillatory movement of the head portion about its longitudinal axis. A particular driving mechanism includes a flywheel having a drive pin which is received in a cam block secured to the drive shaft. The brush head portion comprises a pair of opposed bristle head portions arranged so as to present two groups of opposed bundles of bristles disposed substantially perpendicularly each to the other. Each of the groups of bundles of bristles comprises a plurality of rows and a plurality of columns of bristle bundles, where the rows aligned parallel to the longitudinal axis of the brush head portion, and the columns are aligned perpendicular to the longitudinal axis of the brush head portion. The bristles in each bundle in each row of bristle bundles are substantially equal in length, and the lengths of the bristles in each row of bristle bundles on each bristle head portion are progressively longer in each successive row of bristle bundles which is further away from the longitudinal axis of the brush head portion than an adjacent row of bristle bundles which is closer to the longitudinal axis of the brush head portion. The outer ends of the respective row of bristle bundles on each bristle head portion which is closest to the longitudinal axis of the brush head portion are spaced less than 0.100 inch from the outer ends of the respective opposed row of bristle bundles on the other bristle head portion.

22 Claims, 4 Drawing Sheets

MECHANICAL TOOTHBRUSH WITH OPPOSED DUAL HEADS AND HAVING OSCILLATORY MOVEMENT

CROSS-REFERENCE

This application is a Continuation-In-Part Application of application Ser. No. 09/296,631, now U.S. Pat. No. 6,138,310, filed Apr. 23, 1999, by the same inventors herein.

FIELD OF THE INVENTION

This invention relates to electric toothbrushes, sometimes referred to as mechanical toothbrushes, and is more particularly directed to a portable hand-held, electrically powered, mechanical toothbrush. Specifically, a novel toothbrush head is disclosed.

BACKGROUND OF THE INVENTION

The use of manual toothbrushes has, of course, been know for many years. Indeed, the use of mechanical toothbrushes, typically those which are electrically driven, has been known for a number of years. The purpose, in any event, is to clean the teeth, usually with a toothbrush which comprises a plurality of bristles that are used in conjunction with a dentifrice. Very often, the dentifrice is mildly abrasive.

The dental profession has propounded, for many years, a technique known as the "Bass Technique" which, if properly performed, is said to achieve superior results in terms of cleaning one's teeth using a manual toothbrush. Essentially, the Bass Technique requires the user to position a manual toothbrush over a zone of the teeth, and then to use very short stokes so as to more or less vibrate the brush at that zone where the brush has been located. This short-stroke brushing should continue for a period of time—typically, twenty strokes to forty strokes—so as to remove any foreign material from that zone. The brush is then repositioned and typically another twenty to forty short strokes are performed. Because each zone is very small, the Bass Technique can be very time consuming. Moreover, since it is a requirement that the strokes be very short which, in turn, requires excellent muscle control, exercising the Bass Technique can be very tiring.

The theory is that, at the end of any given stroke, the bristles will flex so as to become oriented in such a manner that the ends of the bristles point generally away from the direction of the travel of the bristles across the teeth. However, at the beginning of the next stroke, in the opposite direction, the still-flexed bristles will then be pointed in the direction of the stroke and this may cause the bristle to chisel the foreign material away from the teeth for a moment before the bristle again begins to flex so as to sweep across the surface of the tooth in the zone where it is located.

However, a more efficacious manner for brushing teeth comprises a variation of the Bass Technique, whereby oscillatory movement is imparted to a toothbrush. Of course, such oscillatory movement is not capable of being executed manually.

A purpose of the present invention is to provide an electromechanical toothbrush—that is, an electrically driven, mechanical toothbrush, most typically referred to as an electric toothbrush which will permit the user to perform a tooth cleaning procedure which improves upon the Bass Technique by imparting oscillatory movement to the toothbrush. In other words, by using the toothbrush of the present invention, the user will be able to locate the toothbrush at a given zone for a short period of time, while executing a plurality of oscillatory motions of the toothbrush to clean the teeth, and then move on to the next zone, thus achieving efficient cleaning of the teeth.

Apart from the removal of leftover food particles and the like, a particular purpose for cleaning the teeth is to remove plaque build-up from the teeth. Typically, when using a manual toothbrush, plaque build-up is removed much more easily from the buccal surfaces of the teeth than from the lingual surfaces of the teeth, with relatively good foreign material removal from the occlusal surfaces of the teeth also being achieved.

One development that has occurred in respect of manual toothbrushes is the provision of twin-headed brushes, whereby the lingual and buccal surfaces of the tooth can be scrubbed using the bristles of the brush at the same time, with the same stroking action of the brush.

As to electric toothbrushes, most electric toothbrushes provide groups of bristles which are located in concentric circles, where the brush head thus provided is rotated or, more usually, it is reciprocally rotated. The co-pending application noted above teaches a toothbrush having twin heads to which a lengthwise reciprocating linear motion is imparted.

DESCRIPTION OF THE PRIOR ART

Several typical prior art toothbrushes are now described. Among them are several manual toothbrushes which comprise dual, opposed bristle heads. They include PORPER U.S. Design Pat. No. D259,977, issued Jul. 28, 1981, which reveals an early design for a toothbrush having opposed bristle heads.

Another manual toothbrush which is adapted for cleaning multiple sides of the teeth at the same time is shown in WAGNER U.S. Pat. No. 5,327,607, issued Jul. 12, 1994. The toothbrush disclosed in that patent includes further bristles which extend from the spine of the toothbrush so as to contact the occlusal surfaces of the teeth at the same as the buccal and lingual surfaces of the teeth are being contacted while the toothbrush is in use.

A typical prior art electric toothbrush is disclosed in AMAKASU U.S. Pat. No. 5,359,747, issued Nov. 1, 1994. Here, a brush member of the toothbrush is given reciprocal motion in the axial direction while, at the same time, the brush member itself is given a rotary motion. The rotary brush member is rotatably mounted on the end of an attachment connected to a drive shaft, and the reciprocating motion in the axial direction thereof is converted into a rotary motion and transmitted to the rotary brush member by a second transmission mechanism.

Another typical prior art electric toothbrush is disclosed in BAUMAN U.S. Pat. No. 5,353,460, issued Oct. 11, 1994. Here, there is a pair of brush elements with driving mechanism which drives one of the brush elements in oscillation, with linkage between the brush elements so that the second brush element is also driven in oscillation. The two brush elements are preferably oscillated in opposite directions. However, the two brush elements can only contact any one surface of the teeth at a time.

A mechanical toothbrush which is said to effectively replicate the Bass Technique is STANSBURY U.S. Pat. No. 5,259,083, issued Nov. 9, 1993. This power driven mechanical toothbrush comprises a plurality of tuft blocks which are mounted on a cam shaft. The tuft blocks are received in sliding relation in a toothbrush head member, and each tuft block slides linearly in a direction parallel to the longitudinal tuft axis as it is guided by guide rails within the head member between a retracted position and an extended position. The tuft blocks are each driven by the rotatable cam. In use, the tuft bristles are brought into contact with the teeth by the user, before the respective tuft block reaches its extended position, so as to thereby flex the bristles and to cause a lateral motion of the distal end of the bristles along the surface of the teeth. This whipping action of the ends of the bristles causes a wiping action across the surface of the teeth while, at the same time, causing a chiselling action by the ends of the bristles against the teeth, so as to thereby remove foreign material away from the teeth in the region where the bristle chiselling action occurs.

Finally, DAUB U.S. Pat. No. 5,027,463, issued Jul. 2, 1991, teaches a toothbrush which may be used for simultaneously brushing and cleaning the occlusal, lingual, and buccal surfaces of the upper and lower teeth of the user. Here, a bristle support member is provided which anchors bristles which extend from the opposite surfaces thereof. The bristles are arranged so that the central rows of bristles are straight while the intermediate and outer rows of bristles on each of the opposed surfaces of the bristle support member are curved. The straight bristles will engage the occlusal surfaces of the teeth, while the intermediate and outer rows will engage the lingual and buccal surfaces of the teeth.

SUMMARY OF THE INVENTION

In accordance with one aspect of the present invention, there is provided an electric toothbrush which comprises a power handle portion and a brush head portion. The power handle portion is adapted to provide a housing for an electric motor and for a driving mechanism which is located at a first end of the power handle portion.

The driving mechanism is powered by the electric motor, and the electric motor has a longitudinal axis. The brush head portion of the toothbrush also has a longitudinal axis which is offset by a first offset distance with respect to the longitudinal axis of the electric motor.

The brush head portion of the toothbrush of the present invention is removably attachable at a first end thereof to the first end of the power handle portion, and the brush head portion comprises a pair of opposed bristle head portions arranged so as to present two groups of opposed bundles of bristles disposed substantially perpendicularly each to the other. Each of the groups of bundles of bristles on each respective bristle head portion comprises a plurality of rows and a plurality of columns of bristle bundles, where the rows of bristle bundles are aligned parallel to the longitudinal axis of the brush head, and the columns of bristles are aligned perpendicular the longitudinal axis of the brush head.

The bristles in each bundle in each row of bristle bundles on each bristle head portion are substantially equal in length. The length of the bristles in the respective row of bristle bundles on each bristle head portion which is closest to the longitudinal axis of the brush head portion is shorter than the length of the bristles in the respective row of bristle bundles on each bristle head portion which is furthest away from the longitudinal axis of the brush head portion. Moreover, the lengths of the bristles in each respective row of bristle bundles on each bristle head portion are progressively longer in each row of bristle bundles which is further away from the longitudinal axis of the brush head portion than an adjacent row of bristle bundles which is closer to the longitudinal axis of the brush head portion.

Typically, the outer ends of the respective row of bristle bundles which is closest to the longitudinal axis of the brush head portion, on each of the bristle head portions, are spaced less than 0.100 inch from the outer ends of the respective opposed row of bristle bundles on the other bristle head portion.

The driving mechanism of toothbrushes in keeping with the present invention comprises a motion translation means for translating rotational driving power from the electric motor to oscillatory motion delivered to the brush head portion. The driving mechanism further comprises a drive shaft which is disposed on the longitudinal axis of the brush head portion of the toothbrush. The drive shaft is adapted to deliver oscillatory driving power from the motion translation means to the brush head portion.

The drive shaft of the driving mechanism is received in a socket in the brush head portion of the toothbrush of the present invention, in a manner so as to receive the drive shaft in position along the longitudinal axis of the brush head portion.

Accordingly, rotational motion of the flywheel is translated by the motion translation means into oscillatory motion of the drive shaft, so as to provide oscillatory movement to the pair of opposed bristle head portions of the brush head.

In keeping with a particular feature of the present invention, as described in greater detail hereafter, the brush head portion comprises two matched halves, and the drive pin. Each of the two matched halves comprises a respective one of the bristle head portions and a respective half of an intermediate arm portion of the brush head portion. Each respective matched half is formed with a portion of the socket at the first end thereof. The socket portion is disposed on the longitudinal axis of the brush head portion. As noted, the drive shaft is received in the socket so that oscillatory driving motion is directly transmitted to the brush head portion.

A further aspect of the present invention is to provide such an electric toothbrush as is described above, where the brush head portion further comprises a collar portion at the first end thereof, which collar portion is adapted to be removably attachable to the first end of the power handle portion. The opposed bristle head portions of the brush head portion are disposed at the end of an intermediate arm portion thereof, which end is opposed to the first end of the brush head portion. The intermediate arm portion is accommodated within the collar portion in such a manner that the drive shaft is received in the socket while being maintained in position on the longitudinal axis of the brush head. This permits replacement of the brush head by a new brush head, or by a different brush head for use by a different user of the toothbrush mechanism of the present application.

A purpose of the present invention is to provide such an electric toothbrush as described above, which can be used to effectively impart the improved version of the Bass Technique to the toothbrush heads and, thereby, to achieve better tooth cleaning results.

Finally, a purpose of the present invention is to bring an electric toothbrush to the market which can be used for very effective cleaning of the teeth, but which can be brought to the market at relatively low cost compared with many of the prior art electric toothbrushes, due to the relatively uncomplicated structure of the electric toothbrush hereof.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

Figure 1:
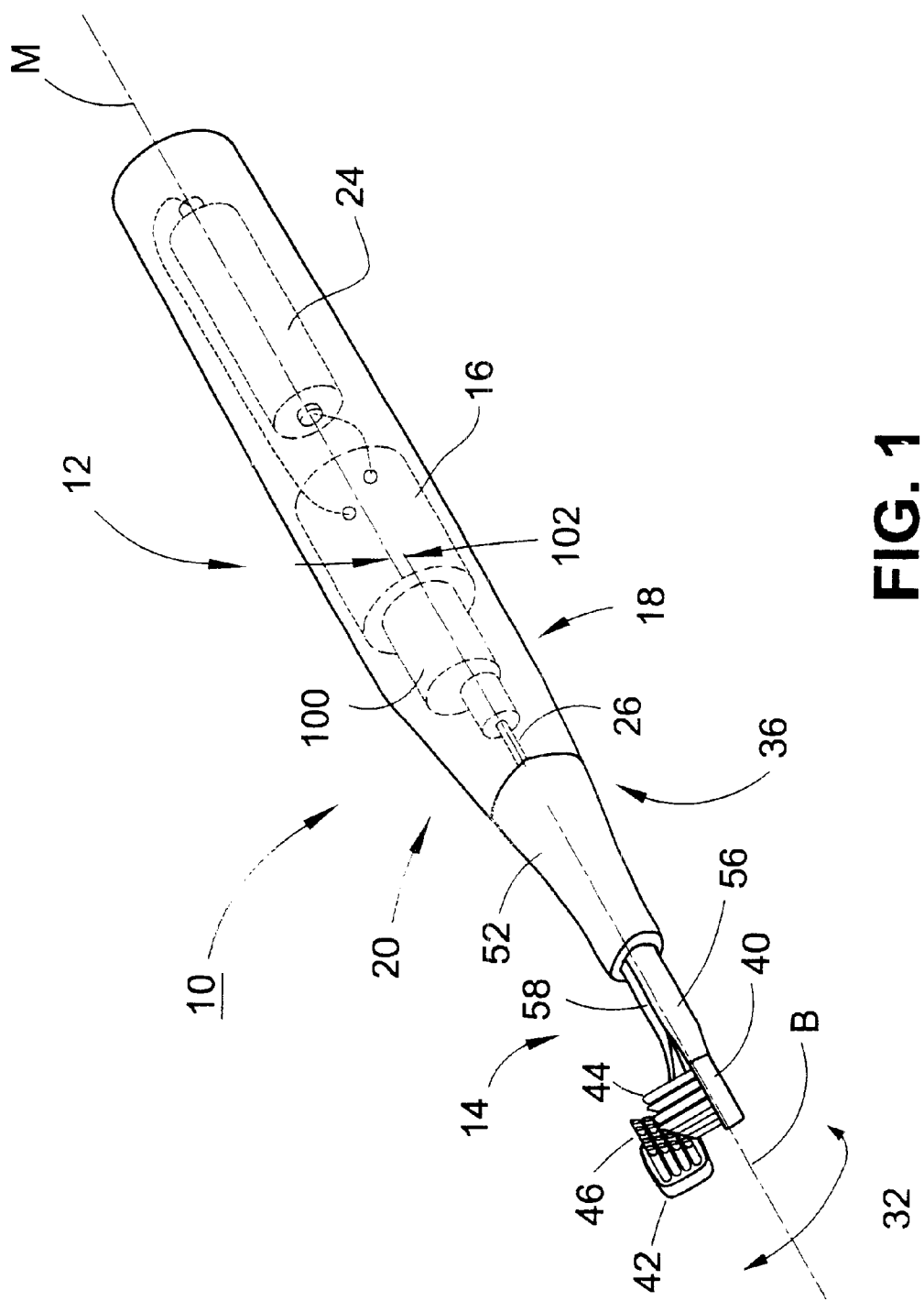
FIG. 1 is a simplified perspective view of a toothbrush in keeping with the present invention, showing several typical power components thereof in ghost fashion.

In a paper published in the *Journal of Clinical Paediatric Dentistry*, Vol. 19, No. 1, Fall 1994, ALMAJED describes the superior results obtained by thirty patients ranging in age between 6.6 and 18 years of age, using a double-headed toothbrush, compared with an ordinary manual toothbrush, with and without dentifrice. The double-headed toothbrush is identified with the trade mark TWINBRUSH™, provided by Prevention Health Products, Inc. of Somers, N.Y., U.S.A., and being that which is identified in Porper U.S. Design Pat. No. D259,977, noted above. The results of the tests were such that, even with manual manipulation of the double-headed toothbrush, it was significantly more effective in removing plaque than the single-headed toothbrush.

The technique used by the patients is identified as being a modified Bass Technique. The results obtained were statistically significant.

As noted above, a feature of the present invention is essentially to provide a double-headed brush head which effectively replicates that which is shown in the Porper design patent, but with a modified arrangement of rows and columns of bunches of bristles in a preferred embodiment and, in any event, arranged in such a manner so as to be mechanically driven as the brush head portion of an electric toothbrush.

A typical configuration of electric toothbrush, in keeping with the present invention, is now described with reference first to FIG. 1. The electric toothbrush 10 comprises a power handle portion 12 and a brush head portion 14. Typically, there is included in the power handle portion 12 an electric motor 16 and a driving mechanism 18, which is driven by the electric motor 16. It will be noted that the driving mechanism 18 is located at or near a first end 20 of the power handle portion 12. It will also be noted that the power handle portion 12 has a longitudinal axis M, which is in fact the longitudinal axis of the electric motor 16.

Typically, the electric motor 16 is a direct current motor. Even more typically, the direct current motor is powered by a battery 24, which is usually a rechargeable battery.

However, it is evident that the electric motor 16 might also be an alternating current motor; or even that the battery 24 might be replaced by a power supply circuit providing low voltage direct current power to the electric motor, whereby the electric toothbrush 10 may be plugged directly into a suitable receptacle. All of those matters are outside the scope of the present invention.

In keeping with the present invention, the driving mechanism 18 includes a drive shaft 26, which has its own longitudinal axis B. The drive shaft 26 is arranged, particularly in a manner described in greater detail hereafter, for coupling to the brush head portion 14 of the electric toothbrush of the present invention. The longitudinal axis B is also the longitudinal axis of the brush head portion 14 of the electric toothbrush of the present invention.

The drive shaft 26 is driven by the electric motor 16 in a manner described hereafter, so as to effect an oscillatory motion of the drive shaft, while it remains in place on the longitudinal axis B. That oscillatory motion will, as described hereafter, result in a concomitant oscillating movement of the brush head portion 14 in a manner as shown by double-headed arrow 32.

The brush head portion 14 is removably attachable at a first end 36 from the first end 20 of the power handle portion 12.

Figure 2:
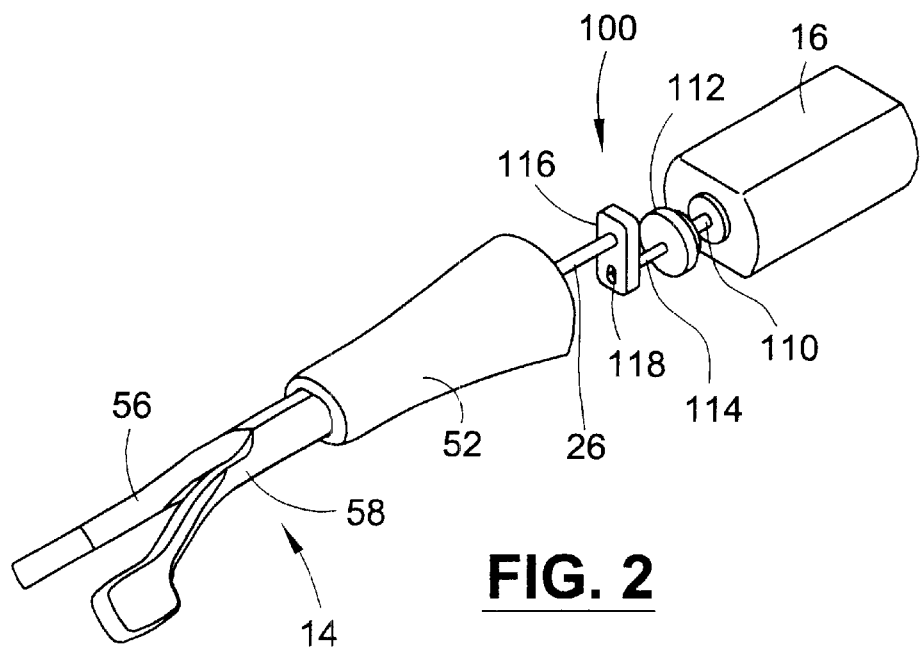
FIG. 2 is a simplified perspective view of a typical drive mechanism in keeping with the present invention.
Figure 3:
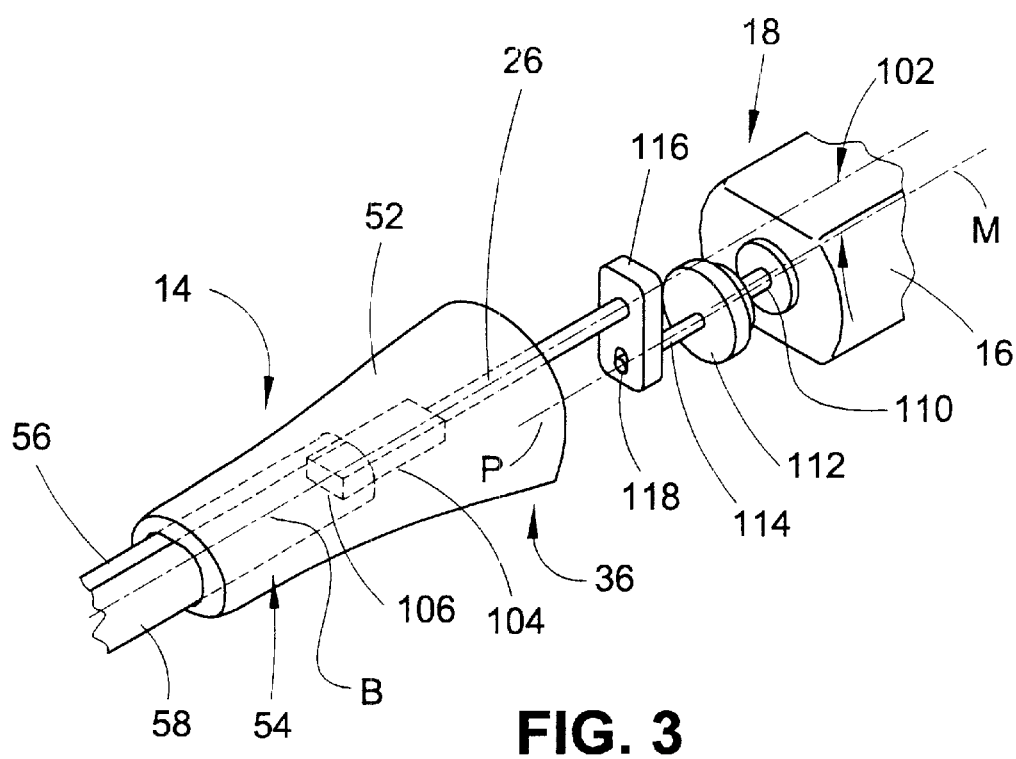
FIG. 3 is similar to FIG. 2, showing a portion thereof to a greater scale, and with additional detail.

Turning now to FIGS. 2 and 3, the following discussion is particularly directed to the drive mechanism 18 and its relationship to the brush head portion 14, and a typical manner in which they are assembled. Further advantages of the assembly of the brush head portion 14, in keeping with a preferred embodiment of the present invention, will be described hereafter.

In general terms, the driving mechanism 18 comprises a motion translation means 100. The generalities of the motion translation means 100 are that rotational driving power from the electric motor 16 is translated to oscillatory motion delivered through the drive shaft 26 to the brush head portion 14. Motion translation means which serve such purposes are well known in the prior art in different areas than those of the present invention; but a particularly effective motion translation means is shown in some detail in FIGS. 2 and 3. It is to be noted, of course, that the longitudinal axis B of the brush head portion 14 is offset from the longitudinal axis M of the electric motor 16, by a first distance indicated by arrows 102 in FIGS. 1 and 3. Since the drive shaft 26 is disposed on the longitudinal axis B of the brush head portion 14, it is necessary for the driving mechanism 18 to deliver the oscillatory driving power to the brush head portion on the longitudinal axis B.

Further details of a typical drive shaft 26 are shown in FIG. 3. Specifically, it will be noted that one end of the drive shaft - the end which is furthest from the driving mechanism 18—is configured or shaped in such a manner that it will impart oscillatory motion to the brush head portion 14. In FIG. 3, that portion 104 of the drive shaft 26 is shown having a square configuration; it might also have a rectangular, hexagonal, or blade-type configuration. In any event, examination of FIG. 3 will indicate that the drive shaft 26 is received in a socket 106 which is formed in the brush head portion 14, so as to receive the drive shaft 26 in such a manner that the drive shaft 26 is secured in position along the longitudinal axis B.

It should be noted that, in any event, the connection between the drive shaft 26 and the brush head portion 14 is such as to preclude any rotational slippage therebetween. Accordingly, an appropriate detachable connection—as discussed hereafter—between the drive shaft 26 and the brush head portion 14 is as indicated in FIG. 3. Obviously, however, any plug and socket or blade and slot connection may be made, where the plug and socket are appropriately shaped, or the blade and slot are appropriately shaped, so that a plug or blade may be slipped into a socket or slot, or the socket or slot may be slipped over the plug or blade. Accordingly, the socket or slot may be formed in either of the drive shaft 26 or the brush head portion 14, with the mating plug or blade being formed in the other of the drive shaft 26 or the brush head portion 14 for co-operating fitment therewith.

Thus, and in any event rotational motion from the motor 16 is translated into oscillatory motion of the drive shaft 26. Because the portion 104 of the drive shaft 26 is not round, neither is the socket 106 into which it is fitted, oscillatory motion is thereby imparted to the brush head portion 14 of the toothbrush of the present invention; and, as noted hereafter, thereby oscillatory movement is imparted to the pair of opposed bristle head portions of the brush head portion 14.

A more specific embodiment of a particular driving mechanism, in keeping with the present invention, is shown in FIGS. 2 and 3. Here, the motor 16 is shown to have a drive shaft 110 on which a flywheel 112 is mounted. The flywheel 112 has a rotational axis which is coincident with the longitudinal axis M of the electric motor 16.

However, mounted on the flywheel 112 there is a drive pin 114, and the drive pin 114 rotates with the flywheel 112. There is also a cam block 116 which has slot 118 at a first end thereof, into which the end of the drive pin 114 which is remote from the flywheel 112 is inserted.

It is important to note that the drive pin 114 has a longitudinal axis P, which is offset from the longitudinal axis M of the electric motor 16. Clearly, as indicated in FIG. 3, in particular, the amount of offset of the longitudinal axis P of the drive pin 114 with respect to longitudinal axis M, is less than the offset indicated by arrows 102 between the longitudinal axis B of the brush head portion 14 and the longitudinal axis M of the electric motor 16.

Obviously, as the flywheel 112 rotates, the end of the drive pin 114 moves back and forth within the slot 118, causing the cam block 116 to swing from side to side, and thereby imparting an oscillatory movement to the drive shaft 26.

Accordingly, since the end 104 of the drive shaft 26 is received in the socket 106—or there is such other connection which is such as to preclude rotation slippage between the drive shaft 26 and the brush head portion 14, as noted above—the relationship between the drive shaft 26 and the brush head portion 14 is such that oscillatory motion transfer will be attained. Thus, oscillatory movement of the brush head portion of the toothbrush in keeping with the present invention will occur.

Typically, the amount of oscillatory motion imparted by the drive shaft 26 to the brush head portion 14 and the bristle head portions thereon, as described hereafter, is in the range of the 3° to 10°—that is, 1.5° to 5° from each side of a neutral position. An oscillatory motion in the range of from 5° to 6° has been found to be quite effective.

Likewise, the rate of oscillatory movement of the drive shaft 26 is typically in the range of from 1,000 to 3,000 reciprocations per minute. Again, 1,500 to 2,000 reciprocations per minute has been found to be quite effective.

Figure 4A:
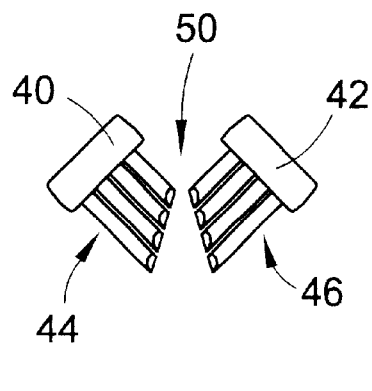
FIGS. 4A, 4B, 5, and 6 are end views of the brush head portion of the toothbrush, and of the brush head portion of the toothbrush being in contact with a typical tooth at the rear of the mouth, and in contact with a typical tooth at the front of the mouth, respectively.

The brush head portion 14 comprises a pair of opposed bristle head portions 40 and 42. The bristle head portions 40 and 42 are arranged so as to present two groups of opposed bundles of bristles, indicated at 44 and 46; and the groups of opposed bundles of bristles 44 and 46 are disposed substantially perpendicularly each to the other as shown particularly in FIG. 4A and FIG. 4B.

Figure 4B:
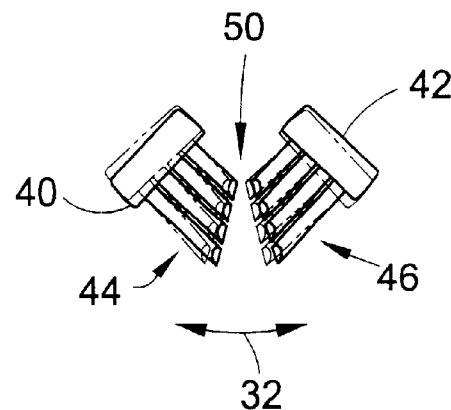

Obviously, FIG. 4B shows the effect of the oscillatory motion of the bristle head portions 40 and 42. One position of those heads is shown in dotted line in FIG. 4B.

Figure 7B:
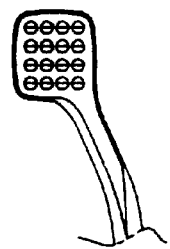
Figure 7C:
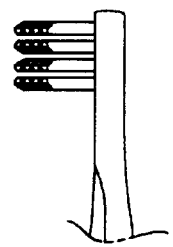
Figure 8A:
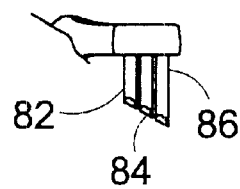
Figure 8B:
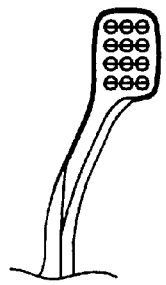
Figure 8C:
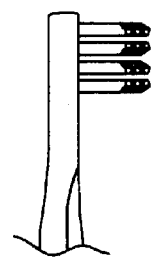

Each of the groups of bundles of bristles on each of the respective bristle head portions 40 and 42 comprises a plurality of rows and a plurality of columns of bristle bundles. For example, FIG. 7B shows four rows and four columns of bristle bundles, whereas FIG. 8B shows three rows and four columns of bristle bundles. It is obvious, therefore, that the rows of bristle bundles are aligned parallel to the longitudinal axis B of the brush head portion 14, and the columns of bristle bundles are aligned perpendicular to the longitudinal axis B of the brush head portion 14.

Figure 7A:
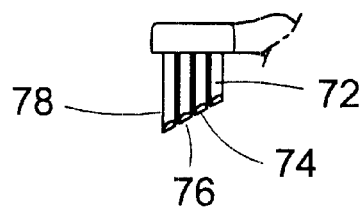
FIGS. 7A, 7B, 7C, and 8A, 8B, and 8C are end, plan, and elevational views, respectively, of two typical configurations of the bristle head portion of a toothbrush in keeping with the present invention.

Moreover, it is seen in each of FIGS. 4A, 4B, 7A, and 8A, in particular, that the bristles in each bundle in each row of bristle bundles on each bristle head portion 40 or 42 are substantially equal in length. Still further, it is evident from an inspection of the Figures of drawings, particularly FIGS. 4A, 4B, 7A, and 8A, that the length of the bristles in the respective row of bristle bundles on each of the bristle head portions 40 and 42 which is closest to the longitudinal axis of the brush head portion 14, is shorter than the length of the bristles in the respective row of bristles bundles on each bristle head portion 40 and 42 which is furthest away from the longitudinal axis of the brush head portion 14. Thus, for example, the length of the bristle bundles 72 shown in FIG. 7A is shorter than the length of each of the bristle bundles 78. The same conditions apply with respect to bristle bundles 82 and 86 shown in FIG. 8A.

Still further, the lengths of the bristles in each of the intervening rows of bristle bundles on each bristle head portion are progressively longer in each row of bristle bundles which is further away from the longitudinal axis of the brush head portion than an adjacent row of bristle bundles which is closer to the longitudinal axis of the brush head portion. Thus, the length of the bristle bundles 72 is shorter than the length of the bristle bundles 74 which, in turn, is shorter than the length of the bristle bundles 76, which is shorter again than the length of the bristle bundles 78, all as seen in FIG. 7A. Likewise, the length of the bristle bundles 84, shown in FIG. 8A, is intermediate to the lengths of the bristle bundles 82 and 86.

Typically, the longest bristles 78 or 86 will range in length from about 0.375 inch up to about 0.45 inch, although those dimensions are exemplary only. Also, as typical examples, the length of a bristle head portion having four columns of bristle bundles may be slightly less than one-half inch; whereas the width of a bristle head portion having four row of bristle bundles, as shown in FIG. 7B, might be in the range of 0.45 inch, while the width of a bristle head portion having only three rows of bristle bundles, such as that shown in FIG. 8B, may be in the range of 0.365 inch.

As will be described in greater detail hereafter, the inner rows of bristle bundles—that is, the rows of bristle bundles which are closest to the longitudinal axis of the brush head portion 14—are arranged so that the outer ends or tips of the bristle bundles are nearly touching each other, as can be seen particularly in FIG. 4. The gap 50 which is between the outer ends of the respective rows of bristle bundles which are closest to the longitudinal axis of the brush head portion, and each of the bristle head portions 40 and 42, may typically be less than 0.100 inch, but may be more or less than that dimension.

Thus, it can be seen that, when the electric toothbrush 10 is turned on by a switch (not shown) and the electric motor 16 drives the driving mechanism 18 and the drive shaft 26 to impart an oscillatory motion to the drive shaft 26, each of the opposed bristle head portions 40 and 42 will undergo an oscillatory movement as indicated by the double-headed arrow 32 in FIGS. 1 and 4B.

Referring again to FIGS. 1 through 3, the brush head portion 14 is seen to further comprise a collar portion 52. The collar portion 52 includes the first end 36 of the brush head portion 14, and is adapted to be removably attachable to the first end 20 of the power handle portion 12. Typically, that attachment is a slide or snap fitment, and is such as to protect the area where the drive shaft 26 is received in the socket 106, or such other plug and socket or blade and slot detachable connection as may be employed. However, it will be evident that the bristle head portion 42 and an intermediate arm portion 54 of the brush head portion 14 are freely moveable in an oscillatory manner about the longitudinal axis B of the brush head portion 14, within the collar portion 52. The opposed bristle head portions 40 and 42 are disposed at the end of the intermediate arm portion 54 which is opposite the first end 36 of the brush head portion 14. As noted, the intermediate arm portion 54 is accommodated within the collar portion 52 in such a manner as to be free for oscillatory motion relative to the collar portion 52, about the longitudinal axis B of the brush head portion 14.

Referring to FIG. 1 through 3, the assembly of the brush head portion 14 is described. It will be seen that the brush head portion 14 typically comprises two matched halves 56 and 58. Each of the matched halves 56 and 58 is, essentially, a mirror image of the other; and each comprises a respective one of the bristle head portions 40 and 42 and a respective half of the intermediate arm portion 54.

In the particular embodiment being illustrated and discussed, it will be seen that in each of the respective matched halves 56 and 58, a portion of the socket 106 is formed at the first end 36, in each respective half of the intermediate arm portion 54.

Generally, the matched halves 56 and 58 of the brush head portion are assembled to each other by being sonically welded to each other. However, they may also be easily glued to each other. This is especially true when, as is typical, the material from which the two matched halves 56 and 58 of the brush head portion have been manufactured is ABS (acrylonitrile butadiene styrene). This factor becomes important when it is considered that a typical material from which the drive shaft 26 is manufactured, is nylon. The drive shaft 26 may also be formed of stainless steel. The drive pin 114, the flywheel 112, and the cam block 116, may also be formed of nylon, stainless steel, or other suitable materials known to those skilled in the art.

It is evident that the manufacture of a double-headed toothbrush may be very easily arranged. Specifically, the bristle head portions 40 and 42 may be populated with the bristle bundles, the ends of the bristle bundles trimmed and rounded, and whatever other manufacturing step is required for the bristles may be attended to, without any regard to the opposed bristle head. This is because the matching halves 56 and 58 are, obviously, separately molded. Previously, double-headed toothbrushes such as that shown in Porper Design Pat. No. D259,977, were molded flat, and the bristle head portions were populated with bristle bundles, trimmed and end-rounded, but with some difficulty due to the close proximity of the other bristle head. Thereafter, the respective bristle head portions were required to be bent or post-formed using heat and, thus, their alignment and spatial relationship with each other is less exact than can be accomplished by the present invention where the matched halves 56 and 58 are manufactured separately and merely require to be assembled to each other, as described above.

Figure 5:
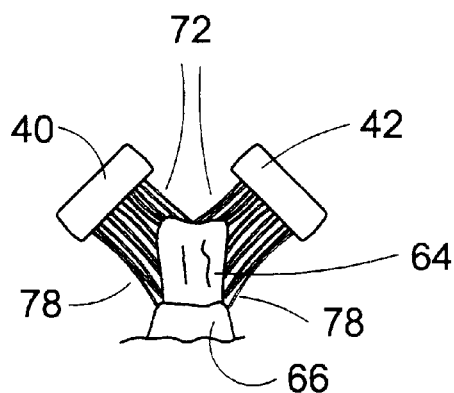
Figure 6:
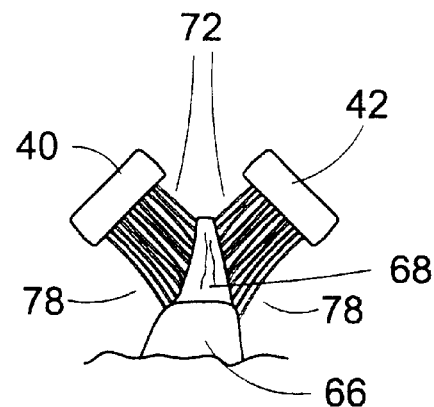

Finally, referring to FIGS. 5 and 6, the advantage of the present invention will become obvious. In FIG. 5, a typical molar 64 is shown together with its supporting gum structure 66. It is seen that the inner bristle bundles 72 on the respective bristle head portions 40 and 42 engage and will clean the occlusal surface of the tooth 64, whereas the remaining bristle bundles will engage and clean the buccal and lingual surfaces of the tooth 64. The oscillatory movement is, as noted above, only in the range of 3° to 10°, and at a rate of 1,000 to 3,000 oscillations pr minute. Thus, the ends of the bristle bundles will be bent and will be constantly changing directions. They will, therefore, probe around the occlusal, buccal, and lingual surfaces of the tooth, and the probe will be effected with limited but effective chiselling action.

Indeed, it is believed that use of many typical prior art electric toothbrushes, particularly those which cause a sweeping motion either rotationally or longitudinally, particularly when combined with the use a typical abrasive dentifrice, actually causes thinning of the tooth enamel. Thus, the rapid but very short strokes of the toothbrush of the present invention are much less likely to cause enamel thinning or other damage to the teeth while, at the same time, providing a more efficient cleaning action due to the short stroke and the constantly changing direction of motion of the bristle ends.

The same conditions are noted in FIG. 6, where a typical front tooth 68 is shown, having its buccal and lingual surfaces cleaned, as well as its occlusal surface to the extent that such surface exists.

It is evident that there is no necessity for there to be any great amount of pressure applied by the user in pressing the bristles of the bristle head portions against the teeth. Moreover, if more than sufficient pressure is applied, this may result in slowing down of the electric motor 16.

There has been described an electric toothbrush which exhibits obvious advantages over prior art electric toothbrushes, and which particularly provides an apparatus which improves upon the highly promoted Bass Technique for brushing the teeth. The precise materials of the bristles and their manufacture are well know to the industry, as is the provision of a suitable power handle portion having an appropriate electric motor and linear reciprocating motion drive shaft. However, their application to an electric toothbrush in keeping with the present invention falls within the scope of the accompanying claims.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

What is claimed is:

1. An electric toothbrush comprising a power handle portion and a brush head portion;

said power handle portion being adapted to provide a housing for an electric motor and for a driving mechanism located at a first end of said power handle portion;

said driving mechanism being powered by said electric motor, said electric motor having a longitudinal axis;

said brush head portion having a longitudinal axis which is offset by a first offset distance with respect to the longitudinal axis of said electric motor;

said brush head portion being removably attachable at a first end thereof to said first end of said power handle portion;

said brush head portion comprising a pair of opposed bristle head portions arranged so as to present two groups of opposed bundles of bristles disposed substantially perpendicularly each to the other;

each of said groups of bundles of bristles on each respective bristle head portion comprising a plurality of rows and a plurality of columns of bristle bundles;

said driving mechanism comprising motion translation means for translating rotational driving power from said electric motor to oscillatory motion delivered to said brush head portion;

wherein said driving mechanism further comprises a drive shaft disposed on said longitudinal axis of said brush head portion, and being adapted to deliver oscillatory driving power from said motion translation means to said brush head portion;

said drive shaft being detachably connected to said brush head portion in a manner so as to preclude rotational slippage therebetween, and so as to secure said drive shaft in position along said longitudinal axis thereof;

whereby rotational motion of said electric motor is translated by said motion translation means into oscillatory motion of said drive shaft, so as to provide oscillatory movement to said pair of opposed bristle head portions of said brush head.

2. The electric toothbrush of claim 1, wherein the detachable connection between said drive shaft and said brush head portion is by way of a socket or slot being formed in one of said drive shaft and said brush head portion and a mating plug or blade being formed in the other of said drive shaft and said brush head portion for co-operating fitment therewith.

3. The electric toothbrush of claim 2, wherein said brush head portion further comprises a collar portion at the first end thereof, which is adapted to be removably attachable to the first end of said power handle portion, wherein said opposed bristle head portions are disposed at the end of an intermediate arm portion which is opposite said first end of said brush head portion, and wherein said intermediate arm portion is accommodated within said collar portion and includes said socket disposed on said longitudinal axis thereof.

4. The electric toothbrush of claim 1, wherein the amount of oscillatory motion by said opposed bristle head portions of said brush head portion about the longitudinal axis thereof is in the range of 3° to 10°.

5. The electric toothbrush of claim 5, wherein the amount of oscillatory motion is in the range of 5° to 6°.

6. The electric toothbrush of claim 1, wherein the rate of oscillatory movement by said opposed bristle head portions of said brush head portion about the longitudinal axis thereof is in the range of 1,000 to 3,000 oscillations per minute.

7. The electric toothbrush of claim 6, wherein the rate of oscillatory movement is in the range of 1,500 to 2,000 oscillations per minute.

8. The electric toothbrush of claim 1, wherein said electric motor is a direct current motor, and said power handle portion further comprises a battery chosen from the group consisting of primary batteries and rechargeable batteries.

9. An electric toothbrush comprising a power handle portion and a brush head portion;

said power handle portion being adapted to provide a housing for an electric motor and for a driving mechanism located at a first end of said power handle portion;

said driving mechanism being power by said electric motor, said electric motor having a longitudinal axis;

said brush head portion having a longitudinal axis which is offset by a first offset distance with respect to the longitudinal axis of said electric motor;

said brush head portion being removably attachable at a first end thereof to said first end of said power handle portion;

said brush head portion comprising a pair of opposed bristle head portions arranged so as to present two groups of opposed bundles disposed substantially perpendicularly each to the other;

each of said groups of bundles of bristles on each respective bristle head portion comprising a plurality of rows and a plurality of columns of bristle bundles;

said driving mechanism comprising a flywheel mounted on a drive shaft from said electric motor so as to have a rotational axis coincident with the longitudinal axis thereof, a drive pin mounted on said flywheel and rotatable therewith, a cam block having a slot at a first end thereof into which the end of said drive pin which is remote from said flywheel is inserted, and an oscillating drive shaft mounted at a second end of said cam block remote from said first end and being adapted for oscillatory motion transfer fitment to said brush head portion;

said drive pin having a longitudinal axis which is offset from said longitudinal axis of said electric motor by an amount less than said first offset distance;

said drive shaft being detachably connected to said brush head portion in a manner so as to preclude rotational slippage therebetween, and so as to secure said drive shaft in position along said longitudinal axis thereof;

whereby rotational motion of said flywheel is translated by movement of said drive pin in said slot of said cam block into oscillatory motion of said drive shaft, so as to provide oscillatory movement to said pair of opposed bristle head portions of said brush head.

10. The electric toothbrush of claim 9, wherein the detachable connection between said drive shaft and said brush head portion is by way of a socket or slot being formed in one of said drive shaft and said brush head portion and a mating plug or blade being formed in the other of said drive shaft and said brush head portion for co-operating fitment therewith.

11. The electric toothbrush of claim 10, wherein said brush head portion further comprises a collar portion at the first end thereof, which is adapted to be removably attachable to the first end of said power handle portion, wherein said opposed bristle head portions are disposed at the end of an intermediate arm portion which is opposite said first end of said brush head portion, and wherein said intermediate arm portion is accommodated within said collar portion and includes said socket disposed on said longitudinal axis thereof.

12. The electric toothbrush of claim 11, wherein said brush head portion comprises two matched halves;

wherein each of said two matched halves comprises a respective one of said bristle head portions and a respective half of said intermediate arm portion;

wherein each respective matched half is formed with a portion of said socket at said first end thereof in each said respective half of said intermediate arm portion.

13. The electric toothbrush of claim 12, wherein the material from which each of said two matched halves has been manufactured is ABS, and the material from which said drive shaft has been manufactured is nylon; and wherein said matched halves of said brush head portion are assembled to each other by the process chosen from the group consisting of gluing said matched halves to each other and sonically welding said matched halves to each other.

14. The electric toothbrush of claim 9, wherein the rows or bristle bundles of each of said groups of bundles of bristles are aligned parallel to the longitudinal axis of said brush head portion, and the columns of bristle bundles are aligned perpendicular to the longitudinal axis of said brush head portion; and wherein the bristles in each bundle in each row of bristle bundles on each bristle head portion are substantially equal in length, where the length of the bristles in the respective row of bristle bundles on each bristle head portion which is closest to the longitudinal axis of said brush head portion is shorter than the length of the bristles in the respective row of bristle bundles on each bristle head portion which is furthest away from the longitudinal axis of said brush head portion, and wherein the lengths of the bristles in each respective row of bristle bundles on each bristle head portion are progressively longer in each row of bristle bundles which is further away from the longitudinal axis of said brush head portion than an adjacent row of bristle bundles which is closer to the longitudinal axis of said brush head portion.

15. The electric toothbrush of claim 9, wherein the amount of oscillatory motion by said opposed bristle head portions of said brush head portion about the longitudinal axis thereof is in the range of 3° to 10°.

16. The electric toothbrush of claim 15, wherein the amount of oscillatory motion is in the range of 5° to 6°.

17. The electric toothbrush of claim 9, wherein the rate of oscillatory movement by said opposed bristle head portions of said brush head portion about the longitudinal axis thereof is in the range of 1,000 to 3,000 oscillations per minute.

18. The electric toothbrush of claim 17, wherein the rate of oscillatory movement is in the range of 1,500 to 2,000 oscillations per minute.

19. The electric toothbrush of claim 9, wherein said electric motor is a direct current motor, and said power handle portion further comprises a battery chosen from the group consisting of primary batteries and rechargeable batteries.

20. An electric toothbrush comprising a power handle portion and a brush head portion;

said power handle portion being adapted to provide a housing for an electric motor and for a driving mechanism located at a first end of said power handle portion;

said driving mechanism being powered by said electric motor, said electric motor having a longitudinal axis;

said brush head potion having a longitudinal axis which is offset by a first offset distance with respect to the longitudinal axis of said electric motor;

said brush head portion being removably attachable at a first end thereof to said first end of said power handle portion;

said brush head portion comprising a pair of opposed bristle head portions arranged so as to present two groups of opposed bundles of bristles disposed substantially perpendicularly each to the other;

each of said groups of bundles of bristles on each respective bristle head portion comprising a plurality of rows and a plurality of columns of bristle bundles, wherein the rows of bristle bundles of each of said groups of bundles of bristles are aligned parallel to the longitudinal axis of said brush head portion, and the columns of bristle bundles are aligned perpendicular to the longitudinal axis of said brush head portion;

wherein the bristles in each bundle in each row of bristle bundles on each bristle head portion are substantially equal in length, where the length of the bristles in the respective row of bristle bundles on each bristle head portion which is closest to the longitudinal axis of said brush head portion is shorter than the length of the bristles in the respective row of bristle bundles on each bristle head portion which is furthest away from the longitudinal axis of said brush head portion, and wherein the lengths of the bristles in each respective row of bristle bundles on each bristle head portion are progressively longer in each row of bristle bundles which is further away from the longitudinal axis of said brush head portion than an adjacent row of bristle bundles which is closer to the longitudinal axis of said brush head portion;

said driving mechanism comprising motion translation means for translating rotational driving power from said electric motor to oscillatory motion delivered to said brush head portion;

wherein said driving mechanism further comprises a drive shaft disposed on said longitudinal axis of said brush head portion, and being adapted to deliver oscillatory driving power from said motion translation means to said brush head portion;

said drive shaft being detachably connected to said brush head portion in a manner so as to preclude rotational slippage therebetween, and so as to secure said drive shaft in position along said longitudinal axis thereof;

whereby rotational motion of said electric motor is translated by said motion translation means into oscillatory motion of said drive shaft, so as to provide oscillatory movement to said pair of opposed bristle head portions of said brush head.

21. An electric toothbrush comprising a power handle portion and a brush head portion;

said power handle portion being adapted to provide a housing for an electric motor and for a driving mechanism located at a first end of said power handle portion;

said driving mechanism being powered by said electric motor, said electric motor having a longitudinal axis;

said brush head portion having a longitudinal axis which is offset by a first offset distance with respect to the longitudinal axis of said electric motor;

said brush head portion being removably attachable at a first end thereof to said first end of said power handle portion;

said brush head portion comprising a pair of opposed bristle head portions arranged so as to present two groups of opposed bundles of bristles disposed substantially perpendicularly each to the other;

each of said groups of bundles of bristles on each respective bristle head portion comprising a plurality of rows and a plurality of columns of bristle bundles;

said driving mechanism comprising motion translation means for translating rotational driving power from said electric motor to oscillatory motion delivered to said brush head portion;

wherein said driving mechanism further comprises a drive shaft disposed on said longitudinal axis of said brush head portion, and being adapted to deliver oscillatory driving power from said motion translation means to said brush head portion;

said drive shaft being detachably connected to said brush head portion in a manner so as to preclude rotational slippage therebetween, and so as to secure said drive shaft in position along said longitudinal axis thereof;

wherein the detachable connection between said drive shaft and said brush head portion is by way of a socket or slot being formed in one of said drive shaft and said brush head portion and a mating plug or blade being formed in the other of said drive shaft and said brush head portion for co-operating fitment therewith;

wherein said brush head portion further comprises a collar portion at the first end thereof, which is adapted to be removably attachable to the first end of said power handle portion, wherein said opposed bristle head portions are disposed at the end of an intermediate arm portion which is opposite said first end of said brush head portion, and wherein said intermediate arm portion is accommodated within said collar portion and includes said socket disposed on said longitudinal axis thereof;

whereby rotational motion of said electric motor is translated by said motion translation means into oscillatory motion of said drive shaft, so as to provide oscillatory movement to said pair of opposed bristle head portions of said brush head; and wherein said brush head portion comprises two matched halves;

wherein each of said two matched halves comprises a respective one of said bristle head portions and a respective half of said intermediate arm portion;

wherein each respective matched half is formed with a portion of said socket at said first end thereof in each said respective half of said intermediate arm portion.

22. The electric toothbrush of claim 21, wherein the material from which each of said two matched halves has been manufactured is ABS, and the material from which said drive shaft has been manufactured is nylon; and wherein said matched halves of said brush head portion are assembled to each other by the process chosen from the group consisting of gluing said matched halves to each other and sonically welding said matched halves to each other.

* * * * *